United States Patent
Blake

(10) Patent No.: US 6,425,917 B1
(45) Date of Patent: Jul. 30, 2002

(54) PHAKIC IOL FILM FRAME

(75) Inventor: Larry W. Blake, Coto De Caza, CA (US)

(73) Assignee: Tekia, Irvine, CA (US)

(*) Notice: Subject to any disclaimer, the term of this patent is extended or adjusted under 35 U.S.C. 154(b) by 0 days.

(21) Appl. No.: 09/570,301

(22) Filed: May 12, 2000

(51) Int. Cl.$^7$ .................................................. A61F 2/16
(52) U.S. Cl. .................... 623/6.42; 623/6.44; 623/6.47; 623/901; 623/907
(58) Field of Search ........................ 623/6.38, 6.42, 623/6.43, 6.44, 6.47, 6.5, 6.52, 6.37, 6.46, 6.49

(56) References Cited

U.S. PATENT DOCUMENTS

| | | | |
|---|---|---|---|
| 4,092,743 A | | 6/1978 | Kelman |
| 4,254,509 A | * | 3/1981 | Tennant ........................... 3/13 |
| 4,315,337 A | | 2/1982 | Choyce |
| 4,718,905 A | | 1/1988 | Freeman |
| 5,071,432 A | | 12/1991 | Baikoff |
| 5,141,507 A | | 8/1992 | Parekh |
| 5,201,763 A | * | 4/1993 | Brady et al. ................... 623/6 |
| 5,326,506 A | | 7/1994 | Vanderbilt |
| 5,571,177 A | | 11/1996 | Deacon et al. |
| 5,653,754 A | | 8/1997 | Nakajima et al. |
| 5,674,282 A | | 10/1997 | Cumming |
| 5,716,403 A | | 2/1998 | Tran et al. |

FOREIGN PATENT DOCUMENTS

| | | |
|---|---|---|
| RU | 2120255 C1 * | 10/1998 |
| WO | WO 88/08287 | 11/1988 |
| WO | WO 93/14924 | 8/1993 |
| WO | WO 99/16390 | 4/1999 |
| WO | WO 99/29266 | 6/1999 |

* cited by examiner

Primary Examiner—David H. Wilse
Assistant Examiner—Javier G. Blanco
(74) Attorney, Agent, or Firm—Knobbe, Martens Olson & Bear, LLP

(57) ABSTRACT

A film frame for an IOL has been developed which has the advantages of being lightweight, non-irritating, easily surgically implanted, aesthetically pleasing, and containing plate haptics. This IOL works in the anterior or posterior chamber of the eye for phakic or aphakic lenses and especially in the anterior chamber for phakic refractive lenses where thinner is better and long-term stability is required.

This deformable IOL frame is a haptic system based on a high modulus harder material shaped skeletal frame or plate haptic assembled with low modulus softer elastomeric hinged zones. The rigid frame or haptic in combination with the soft hinges will ensure that the lens is ideally situated in the anterior chamber angle of the eye. Additionally, the soft elastomer can be extended to provide for a softer atraumatic contact point or 'toe' in the eye tissue.

40 Claims, 9 Drawing Sheets

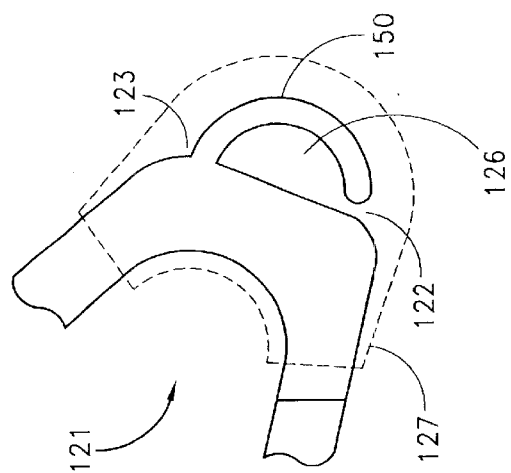
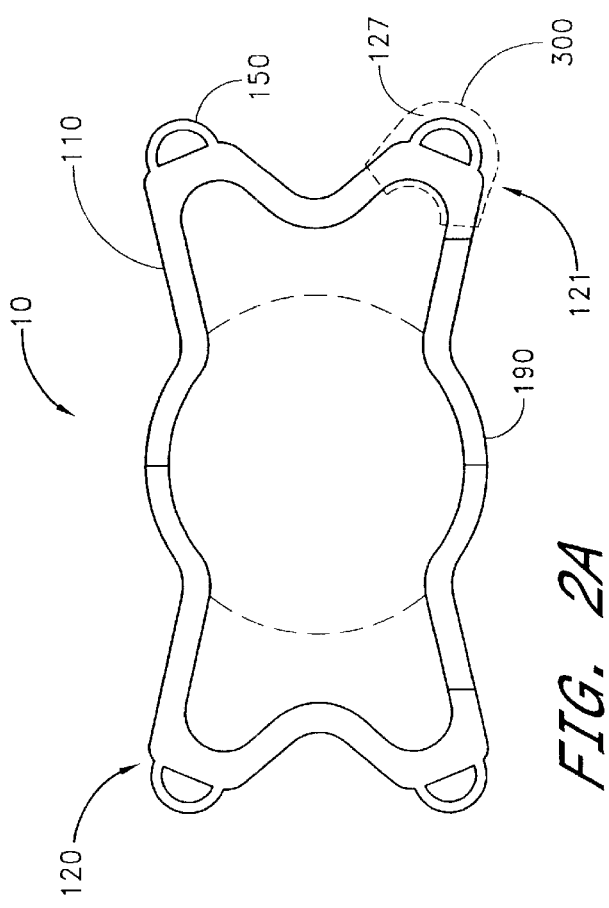
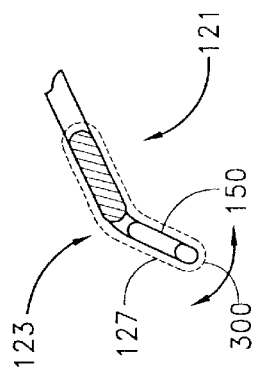
FIG. 2A
FIG. 2B
FIG. 2C

PHAKIC IOL FILM FRAME

FIELD OF THE INVENTION

The present invention generally relates to a deformable IOL haptic system. More specifically, the present invention relates to an IOL incorporating a high modulus shaped skeletal frame assembled with low modulus soft hinged zones.

BACKGROUND OF THE INVENTION

The history of intraocular lenses (IOLs) is a long and varied one. Intraocular lenses can be used to treat a wide diversity of eye conditions ranging from cataracts to any type of eyesight correction. In addition, IOLs can be used to replace an irreversibly damaged lens in the eye—aphakic eyes. Alternatively, the lenses can be used in addition to the natural lens to correct the vision—phakic eyes. These lenses can be placed in the anterior or posterior chambers of the eye.

Early IOL researchers were plagued with problems associated with the materials which were obtainable to them at the time (early 1950's) making the lenses too heavy and too large. Surgery of the eye was in its infancy and therefore there were many problems with the surgical procedures. Since that time the quality, size and weight of the optics as well as microsurgical procedures have dramatically improved.

The earliest IOL's were placed in the anterior chamber of the eye, this being the easiest chamber to get to. Along with the early problems with the optics and surgical techniques, placement of a lens in the anterior chamber proved difficult because the anterior chamber is narrow (about 1.5 to 2.5 mm).

Because of the narrow chamber, an IOL can easily come in contact with the corneal endothelial layer, in which case the nondividing cells may be damaged. If enough damage occurs there may be scarring to the cornea which affects eyesight and can cause 'dark zones'. In addition, the two areas available for fixation (i.e., mechanical support) of the IOLs in the anterior chamber created new problems. The first location for attachment is the iris. However, with such attachment, and since it is necessary to allow for the rather considerable movement and patency of the iris, obstructions could result in uveitis and glaucoma.

The second location is the angle between the cornea and the iris. Angle supported anterior chamber IOLs took advantage of, the anterior chamber angle to support and fix the IOL in place. By angling the IOL into opposite sides of the anterior chamber, the natural angle was used to keep the IOL from moving. However, early lenses experienced marked problems with endothelial loss due to chafing against the early thick lenses. Later lenses were able to reduce the significance of this problem, but still retained problems associated with placement of the IOL in the chamber angle. The biological properties of that angle make it a very sensitive area. The structures associated with equalizing the internal pressure of the eye are located in that area. Additionally, the tissue in the area is easily irritated arid irritation initiates a growth of fibrous tissue; called synechiae. The IOL fixation must be gentle in order to reduce irritation, but stable enough that it will not be easily moveable. This compromise is difficult to obtain. In addition, although the results were excellent in the short-term, there was a significant problem in the long term with altered night vision, loss of endothelial cell populations and alteration of the anterior uvea. These problems as well as the fact that such anteriorly positioned lenses were uncomfortable to the patient, caused many doctors to abandon anterior chamber IOL's.

A third location was developed later and involves implanting a contact lens between the iris and the natural lens. These lenses are called ICL's or implantable contact lenses. However, the ICL's are suspected of initiating cataracts and glaucoma.

As the development of the IOL's became more sophisticated, Ophthalmologists recognized various problems. A typical IOL is composed of an optic, the 'lens' part of the structure, and a mounting mechanism called a haptic. The haptics are the part of the IOL that comes in contact with the eye tissue to hold the lens optic in place. There were essentially two major types of haptics which were developed—fiber and plate haptics. Fiber haptics are slender strands of resilient material which are attached at one end to the optic, and which rest, at their other end, against the eye. Fiber haptics have the advantage of being very light and slender. This would seem to make them ideal by causing less damage to the tissue and additionally being aesthetically pleasing because they are very narrow. The slenderness makes it more difficult for someone looking at the patient to see the IOL through the eye. Plate haptics are formed as a sheet, which has a central opening to support the optic and an outer perimeter which rests against the eye. Because of their size, plate haptics tend to be more easily seen from outside in the patient's eye and the addition of extra material weight to the IOL and reduced flexibility as compared to fiber haptics leads to poor fixation and consequent migration or dislocation of the IOL. While, fiber haptics have the disadvantage of initiating a process in which the body builds fibrous tissue or synechiae around the fiber haptic which immobilizes the iris, the larger plate haptic very rarely, if ever, causes such a reaction.

The adverse problems associated with the earlier anterior chamber haptic designs encouraged the development of IOL's for the posterior chamber for the majority of implants.

SUMMARY OF THE INVENTION

Accordingly, an intraocular lens (IOL) has been developed. The intraocular lens features an optic and a haptic. The haptic features a pair of relatively more rigid elements formed of relatively higher modulus (harder) materials which are flexibly springy when thin and, which are separated from one another at a discontinuity; and a relatively less rigid element formed of relatively lower modulus (softer) material bridging the discontinuity. In one arrangement, the bridged element allows for the relatively more rigid element to be angled to fit into the anterior chamber angle. In a further arrangement the haptic features four separate relatively more rigid elements. The higher modulus springy material may be selected from polyimide (such as KAPTON), polyetheretherketone, polycarbonate, polymethylpentene, polymethylmethyl methacrylate, polypropylene, polyvinylidene fluoride, polysulfone, and polyether sulfone. Preferably, the higher modulus material is polyphenylsulfone (PPSU). Preferably, the higher modulus material has a modulus of elasticity of about 100,000 to about 500,000 psi, even more preferably about 340,000 psi and has a hardness of about 60 to 95 on the shore D scale, but more specifically a Rockwell R hardness of 120 to 130. The lower modulus rubbery material may be an elastomer selected from silicones, urethane, or hydrophilic acrylics. Preferably, the lower modulus material has a modulus of about 100 to about 1000 psi (unit load at 300% elongation).

Preferably, lower modulus material has a hardness of about 15 to 70 on the shore A scale of hardness. Preferably, the lower modulus material is a dispersion such as NUSIL MED 6600, 6605, 6400, or 6820.

In one embodiment, the relatively more rigid elements comprises a frame. The frame forms a haptic which may be formed from a single uniform piece of material. The frame may have a hinge to allow folding of the intraocular lens. In a further embodiment, the frame may have one or more additional haptics. The haptic may contain a slot open on one side to form a hinge which is bendable at the slot. The haptic may alternatively contain a groove to form a hinge which is bendable at the groove.

In one embodiment, the lens and high modulus portions of the haptics may be formed from a single uniform piece of material. The uniform piece of material may be thin and include a thin lens. Alternatively, the uniform piece may be thick (up to about 1 mm thick), but thinner at the haptics, which are preferably less than or equal to about 0.01 inch thick. The haptic may be intentionally broken at the discontinuity. Alternatively, the region of discontinuity may be sculpted down to be so thin that it is flexible. The optic may be a refractive lens, or an interference lens, producing a thin optic. In one embodiment, the haptic is attached to the optic externally. In another embodiment, the lens is attached to the haptic frame using a bridge.

The lower modulus material may partially or completely cover the haptics. In one embodiment, the lower modulus material is extended beyond the tip of the haptic to produce a softer contact point for the eye tissue. The lower modulus material may be applied by first surface treating the higher modulus material and then molding the lower modulus material onto the treated surface. Preferably, the surface treatment is a corona or plasma treatment and additionally a primer. Preferably, the molding is dip molding, cast molding, or injection molding.

The invention is an intraocular lens frame, having two plate haptic elements each including a foot region and a toe region both formed of relatively higher modulus harder material; and a hinge connecting the toe region to the foot region, the hinge being formed of relatively lower modulus material. This can be referred to as a "duplex" material.

Further, the invention is an intraocular lens having an optic; and a haptic including a pair of stiffer elements joined by a flexible element of different material.

Still further, the invention is a method for making an intraocular lens haptic, having the steps of forming a frame, coating a location of the frame, and breaking the frame at the location.

Still further, the invention is a method of mounting a lens in the anterior chamber of an eye, having the steps of supporting a lens on a plate haptic at the angle of the anterior chamber; and bending the haptic at a preferential hinge line to reduce pressure against the angle.

BRIEF DESCRIPTION OF THE DRAWINGS

FIG. 2A is a plan view of the haptic in accordance with the preferred embodiment with an optic shown in phantom lines.

FIG. 2B is an enlarged plan view of the hinge region in accordance with the preferred embodiment.

FIG. 2C is an enlarged side view of the hinge region in accordance with the preferred embodiment.

DETAILED DESCRIPTION OF THE PREFERRED EMBODIMENT

Accordingly, a haptic in the form of a film frame has been developed for an IOL. This film frame haptic is lightweight, springy and arcuate, non-irritating, easily surgically implanted, aesthetically pleasing, and like earlier plate haptics does not support fibrous tissue growth. This IOL works in the anterior or posterior chamber of the eye for phakic or aphakic lenses, but is especially suited for use in the anterior chamber for phakic refractive lenses where thinness is critical and long-term stability is required.

This deformable IOL film frame is a haptic system based on a high modulus, shaped skeletal frame or plate haptic assembled with low modulus, soft, elastomeric hinged zones. The more rigid frame or haptic in combination with the soft hinges ensures that the lens and haptic assembly will maintain its shape and stay ideally situated in the anterior chamber angle of the eye. Whereas, a haptic of a single soft material will not maintain a desirable shape and will be more noodle-like in its action. Additionally, the soft elastomer on the rigid frame can be extended to provide a softer atraumatic contact point or 'lip' which rests against the eye tissue. Lastly, the compliant hinge can automatically adjust to the normal movements of an eye.

Figure 1:
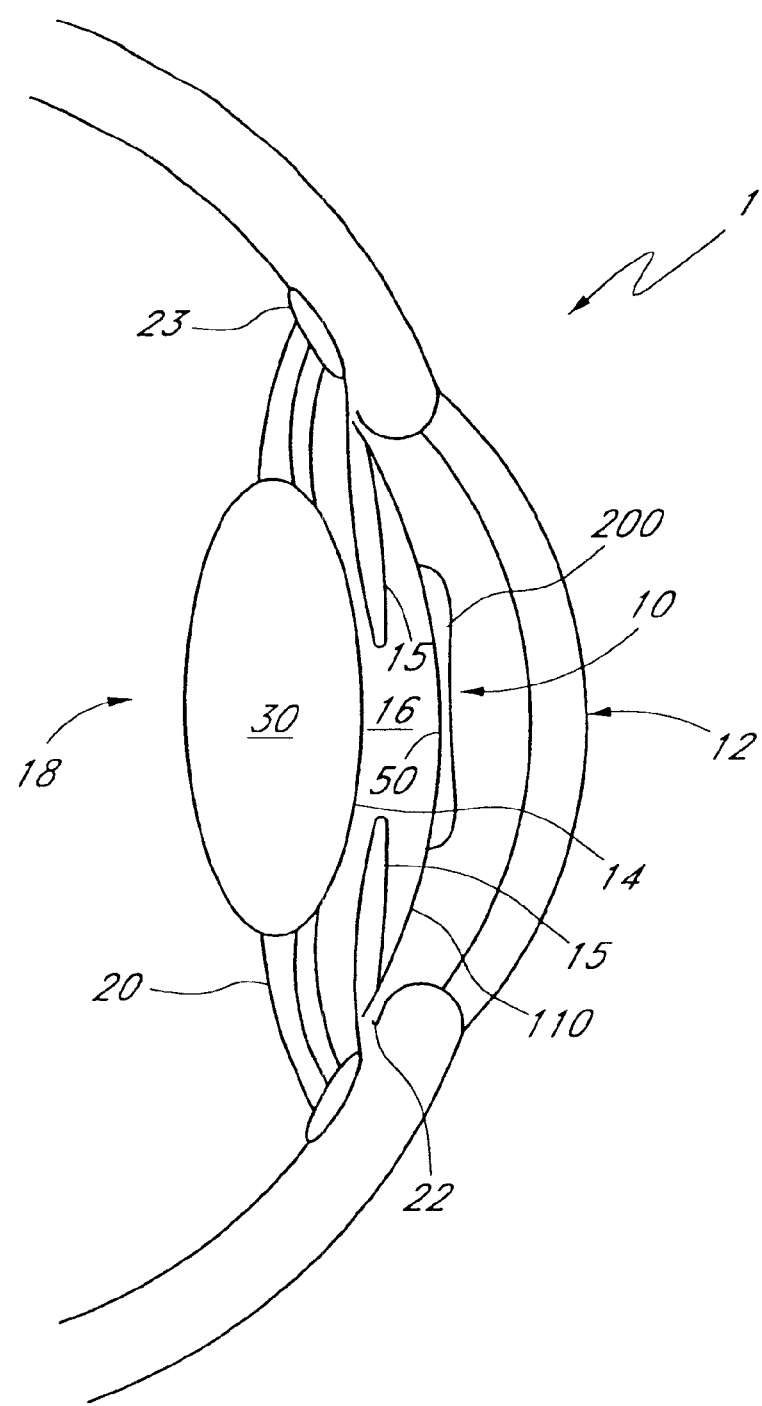
FIG. 1 is a simplified representation of the cross-sectional physiology of the eye with an anterior IOL in accordance with the preferred embodiment implanted.

Referring to FIG. 1, the cornea 12 serves as a refracting medium in addition to its function as the anterior wall of the eye 1. The pupil 14 and the iris 15 of variable aperture are located behind the cornea 12 and divide the eye 1 into an anterior chamber 16 and a posterior chamber 18. The natural crystalline lens 30 is connected by zonular fibers to a peripheral muscle about the lens 30 known as the ciliary muscle 20.

The more standardized procedure for the removal of a diseased natural lens 30 followed by implantation of an artificial lens involves the phakoemulsification of the diseased lens through about a 3 mm (small) incision in the eye and through a capsulorhexis incision in the capsule that encloses the lens in the posterior chamber 18, then an artificial intraocular lens implant is implanted back through the capsulorhexus into the capsular bag. For other types of procedures, the natural lens 30 may not require removal at all. The optic 200 of the IOL 10 used in these procedures includes a centrally located optical zone and may be configured for implantation into either the anterior or posterior chamber 16 or 18 and may be used for either procedure set out above. The haptic 110 of the IOL 10 extends radially outwardly in the general plane of the optic 200.

With reference now to FIGS. 2A–2C, the IOL arranged and configured in accordance with certain features, aspects and advantages of the present invention will be described in detail. FIG. 2A and B are plan views of the film frame haptic of an IOL 10 in accordance with the preferred embodiment. The intraocular lens 10 is generally comprised of a lens optic 200 (shown in phantom lines) and a lens frame haptic 110.

Figure 3A:
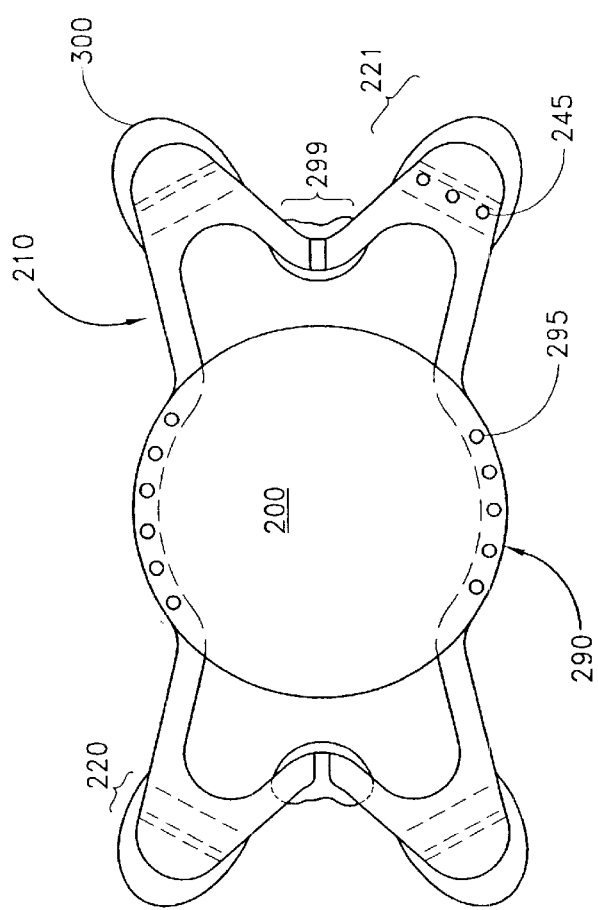
FIG. 3A is a plan view of an alternative embodiment of the haptic in which additional hinges are added to allow folding of the IOL during insertion in the eye.

The lens optic 200 is not shown in this view but is shown in FIG. 3A. The film frame haptic 110 includes four feet 121 and two cross bars 190. It will be seen in further embodiments that the cross bars 190 can alternatively be eliminated through attachment of the feet 121 to the lens optic 200 itself. Each foot 121 has a hinge region 120 which can be configured in a number of ways, but has the property of being more elastic than the main body of the foot 121. This hinge region 120 is formed of a material which is more elastic than the remainder of the lens frame haptic 110. In the preferred embodiment, the hinge region 120 is covered in an elastomeric material 127 which extends between the foot 121 and toe 150. The hinge zone 120 can be a thinner section in the frame, or a discontinuous opening in the frame where the elastomer 127 extends between the foot zone 121 and the toe portion 150. The hinge 120 and toe 150 can be produced in a variety of ways which will be described in detail below. It is envisioned that the hinge 120 and toe 150 could additionally be added to any haptic or frame known by one of skill in the art.

With reference now to FIGS. 3A and B, the lens optic 200 can be any type of lens. However, for use with the anterior chamber IOL, the lens optic 200 is preferably thin to accommodate the narrow space within the anterior chamber. The optic 200 can be a simple refractive lens, a monofocal, toric or aspheric, a bifocal, an interference lens, a positive lens or a negative lens. The lens can be made thinner by using the polychromatic diffractive lens disclosed in U.S. Pat. No. 5,589,982 which is hereby incorporated herein by reference. Optionally a regular lens can be made thinner by edge-bonding, or bonding the haptic to the outside of the lens as disclosed herein rather then burrowing a hole into the side of the lens as is done routinely. The lens optic 200 can be made of silicone (Optical index N=1.40 to 1.46), soft acrylic (N=1.40 to 1.46), hydrophilic acrylic, or methyl methacrylate (N=1.49). Alternatively, the lens optic 200 may be made of the same material as the film frame haptic 210.

In this case the lens optic 200 and frame haptic 210 can be formed from the same plastic film i.e. polyphenylsulphone (PPSU) with a relatively high optical index of 1.674 which is desirable for thin lenses. Alternatively, the lens optic 200 can be made by the method of U.S. Pat. No. 5,589,982 as an interference lens, or may be a diffractive lens or any lens known in the art.

Figure 3B:
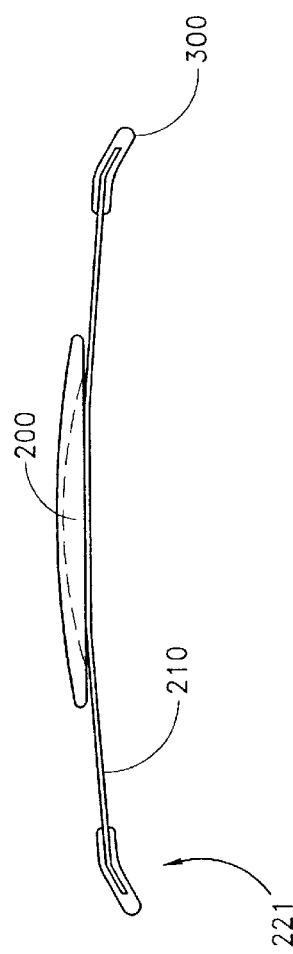
FIG. 3B is a side view of the alternative embodiments of FIG. 3A.

The lens optic 200 can be attached to the frame haptic 210 in a variety of ways. One alternative is shown in FIGS. 3A and 3B, in which the cross bars 290 include holes 295 which permit mechanical attachment of the lens by adhesive. Adhesive bonding typically involves a number of steps. First the film haptic 210 typically undergoes a surface treatment. This treatment is thought to provide active groups for cross-linking or mechanical attachment. The surface treatment may be any known to one of skill in the art such as electrostatic treatments. The treatment may also be a chemical treatment using an acid or base. A method for corona treatment is disclosed in U.S. Pat. No. 5,589,024, herein incorporated by reference. Next a primer is typically applied to allow the adhesive to stick. In the preferred embodiment, the primer is a silicate/acetoxy primer. Lastly, an acetoxy or oxime (RTV), silicone adhesive is applied. Alternatively, the adhesive can be an epoxy such as MASTERBOND epoxy EP21LV, or it can be an acrylate or a urethane adhesive or a solvent ie. Methylene dichloride or N-Methylpyrrolidinone (NP). The lens optic 200 can be attached onto the frame haptic 210 at the top, bottom, or both sides in combination. Alternatively, the frame haptic 210 can be made to be the thickness of the lens optic 200 and bonded to die outside edge of the lens optic 200. As mentioned before, the lens optic 200 may be continuous with the frame haptic 210 and feet 221 by forming the frame haptic 210, feet 221 and lens optic 200 out of a single piece of material.

Figure 4A:
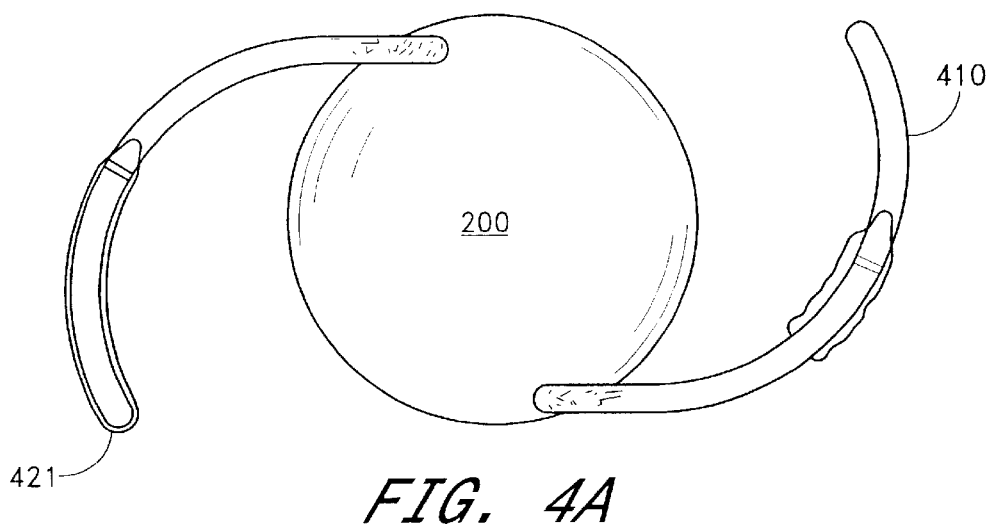
FIG. 4A is a plan view an alternative embodiment of the IOL in which the haptics are separate from the frame and bonded onto the outside of the frame.
Figure 4B:
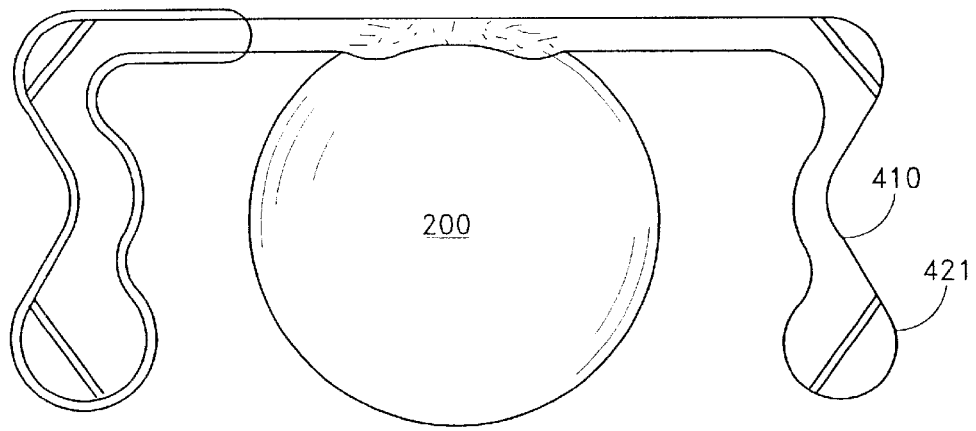
FIG. 4B is a plan. view of an alternative embodiment of the IOL in which the haptics are separate from the frame.
Figure 4C:
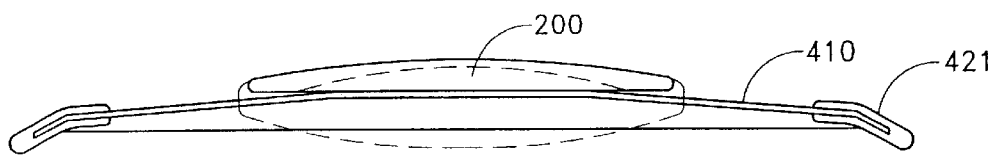
FIG. 4C is a side view of FIG. 4A or 4B.

In one embodiment, shown in FIG. 4A and 4B the haptics 410 are each made separately and attached onto the lens optic 200 by external surface bonding rather than the typical insertion of the haptic into a hole in the lens. Here, the haptics 410 and feet 421 are attached to the lens optic 200 externally on the top or bottom or edges of the lens optic 200 by any of the means described above—mechanically or adhesively, although it should be understood that any method known to one of skill in the art can be used to attach the haptics 410. to the lens optic 200. As used herein it is understood that "attached externally" means that in order to put the haptic on the lens it is moved laterally against the face or edge of the optic 200. To insert a haptic in a hole it must be moved axially "into" a hole or poked into the tens to form a hole.

With reference to FIGS. 2A–2C, the film frame haptics 110 and feet 121 are preferably manufactured from a high modulus material. High modulus materials are generally relatively stiff, or hard, but springy and permit relatively little elongation before they break. Such materials are often brittle and have a high permanent set, but retain their shape after formation. Preferably, the high modulus material is a biocompatible thermoplastic film such as polyimide, polyetheretherketone, polycarbonate, polymethylpentene, polymethylmethyl methacrylate, polypropylene, polyvinylidene fluoride, polysulfone, and polyether or polyphenyl sulfone. These are often referred to as "engineering plastics". They have high tensile strength and are biocompatible, hydrolytically stable, and autoclavable for sterility, and have a high modulus ranging from a tensile modulus of about 100,000 to 500,000 psi (using test method D 638 of the ASTM). The material can be clear, opaque, or tinted, but is preferably clear. However, in many cases, even a tinted material, if produced thinly enough, will appear clear in the eye. The frame 110 and feet 121 may be cut from a sheet by machining, stamping, chemical machining, water jet machining or photomachining with an excimer or YAG laser. The sheet material may also be punch stamped, perforated, photochemically or photooptically shaped. An alternative method for production of the film frame 110 includes molding the high modulus material into the desired shape.

Figure 9A:
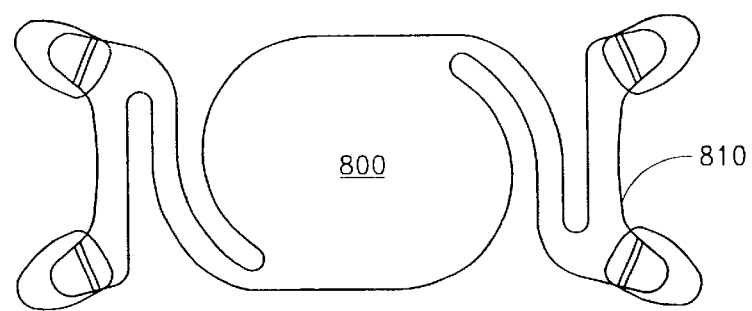
FIG. 9A is a plan view of a preferred embodiment in which the lens and film frame/haptics are formed from a single uniform piece of material.
Figure 9B:
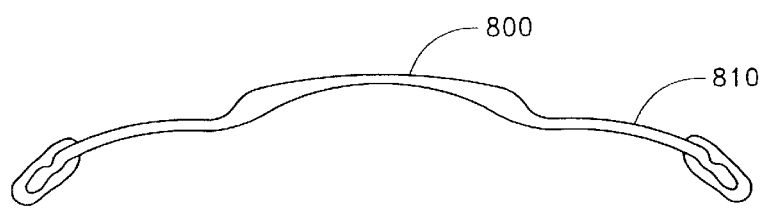
FIG. 9B is a side view of a preferred embodiment in which the lens and film frame/haptics are formed from a single uniform piece of material.

With reference to FIGS. 9A and B, in one embodiment, the lens 800 and film frame/haptic 810 are made from a single uniform piece of material. The piece can be made thin and flat, with a special diffusion or interference surface produced on the material. Alternatively, the piece can be somewhat thicker to produce the lens 800 and the film frame/haptics 810 can be sculpted down to the correct thinness. Sculpting can be done to as little as ¼ of the original thickness by various cutting, polishing or grinding techniques known in the art.

With reference to FIG. 2A–2C, the film frame haptic 110 is typically next polished to remove any rough edges. The preferred method of polishing involves abrasive tumble agitation polishing with glass beads. An alternative method for polishing the film frame haptic 110 and feet 121 includes flame polishing. At least the areas of the film frame or haptic 110 away from the optic region, which are to be hinges, are then treated such that an elastomeric compound can be attached. However, it is understood that a different method may be used to attach the optic 200 to the film frame haptic 110. The preferred surface treatment is that of corona treating. An alternative surface treatment includes plasma (a low pressure corona treatment) treating. Alternatively, the entire frame 110 could be surface treated or primed. Additionally, surface roughening such as by grit or vapor blasting can be included. In the preferred embodiment, the frame haptic 110 is polyphenylsulfone which has a tensile modulus of about 340,000 psi (using test method D 638 of the ASTM) and is clear but exhibits a natural UV light absorbence property below 400 nm's resulting in a yellowish or amber tint without the need to add a UV absorber into the polymer (i.e. benzophenones or benzotriazols). The frame haptic 110 is preferably made from film which is generally ≦0.025 cm (0.010 inches) thick, preferably 0.001 to 0.005 inches thick, but could be as much as 0.012 inches thick. In the preferred embodiment the feet 121 are identical, but, non-identical feet 121 configurations can be paired for use in an alternative embodiment when necessary. The thinness of the film frame haptic 110 contributes to its springiness and lightness which is advantageous in that the IOL is less likely to be disrupted from its initial position.

The film lenses of these designs are typically about half the weight of a standard lens and can be between 2 to 10 milligrams and as low as 1 milligram in weight in air and about 10% of this when in the aqueous of the eye.

With continued reference to FIGS. 2A–C, the film frame/haptic 110 comprises four areas which come in contact with the eye tissue. The feet 121 and toes 150 function like plate haptics and, as such, differ from the fiber haptics of the prior art. This is advantageous because evidence clearly shows that fiber haptics contribute to the problem of synechiae. When the feet 121 and toes 150 sit in the anterior angle 22 of the anterior chamber 16 (see FIG. 1), they come in contact with very sensitive tissue. This tissue reacts to the contact of a fiber-like haptic by producing fibrous tissue around the haptics and "growing" onto the haptics. The fiber-like growths are called synechiae. However, plate haptics do not exhibit this property. Therefore, in reference to FIGS. 2A–C, the feet 121 and toes 150 of the preferred embodiment are shaped like plate haptics. The hinged "toe" 150 is attached to the foot so that will easily rotate to adjust into a better fit while maintaining lens centration.

The feet 121 include a hinge region 120. The hinge region 120 permits each toe 150 to have a relaxed position which can be at a slight angle to the plane of the film frame 110 and the rest of the foot 121, as shown in FIG. 2C. This slight angle permits each foot 121 to fit into the anterior chamber angle 22 in such a way that the IOL 10 will be gently secured using the low mechanical loads produced by the flexible hinge region 120 combined with the flexible frame. The flexible frame can additionally be arcuately curved or shaped with a dihedral angle to more closely approximate the eye shape. More specifically, the toe region 150 is preferably made up of a loop 126 (see FIG. 2B), such that one end of the loop 126, or slotted region, is spaced from the foot 121 to form an opening 122. The other end of the loop 126 is attached to the foot 121 by a notched or thinned region 123, which temporarily supports the loop 126 in place during fabrication.

Alternative embodiments are shown in FIGS. 3A–3B in which the hinge regions 220 are scored into the high modulus material. Alternative attachments apertures 245 can also be included. Further alternative embodiments for the shape of the hinge region 220 and feet 221 are show in FIGS. 5A–F, 6A–B, and 7A–B.

With reference to FIGS. 2A–C, the hinge regions 120 are treated in such a way that a lower modulus material can be coated onto the higher modulus material completely, or partially to connect the toe 150 and foot 121 regions as explained above. The coating for the hinge 120 and toe 150 is made from an elastomeric material which has a lower modulus (rubbery) than that of the harder film frame haptic 110. A low modulus or softer material has high elongation and high memory to urge the toe back into its original position when compressed and is preferably snappy like laytex surgeons gloves. The more rigid frame haptic 110 provides the conforming shape while the elastamer provides a resilient hinge 120, similar to a person's feet and toes. A rubbery hinge connecting rigid frame members functions, such that, when bent, the outer rubbery surface is tensioned and the inner rubbery surface is compressed. A variety of biocompatable elastomers such as urethanes and silicone dispersions such as NUSIL MED 6605, 6400, or 6820 can be used as elastomers for the hinge 120 covering. The high modulus material can be surface treated using corona, plasma, or primers, individually or in combination. Next a primer is applied and lastly, the elastomer or low modulus material can be added by dipping at least each foot 121 into the coating. The low modulus material is mechanically attached or chemically attached, and may be applied by cast molding as well as injection molding. In the preferred embodiment the process can be repeated. For example, the hinge region 120 and foot region 121 are dip coated multiple times. However, alternative embodiments do not require multiple dipping. A protocol for the coating process is included in Example 1.

After coating, the hinge regions 120 may be produced by breaking the high modulus material at the hinges 120, scores 220 (See FIG. 3), or notches 123. This may be done by flexing the region until the high modulus material work hardens and breaks. Alternatively, the hinge region may not need to be broken. With reference to FIGS. 5A–L, in which various embodiments of the foot 121 and toe 150 are presented, FIGS. 5A and B show a typical foot 121 in which there is no hinge 120 shown but an elastomer 127 is applied.

Figure 5A:
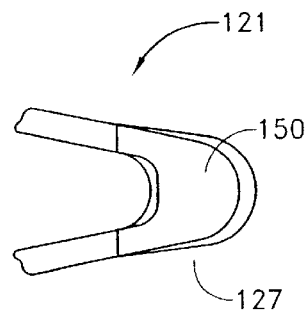
FIGS. 5A–L are plan and side views of a series of steps used to manufacture various embodiments of the hinged region.
Figure 5B:
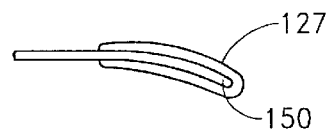
Figure 5C:
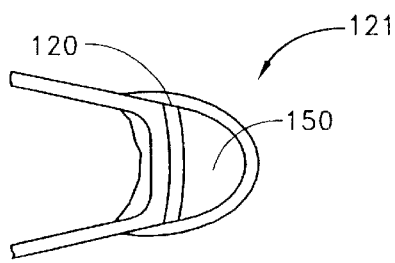
Figure 5D:
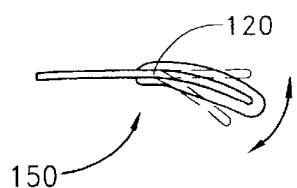
Figure 5E:
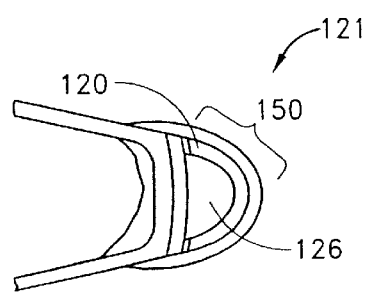
Figure 5F:
Figure 5G:
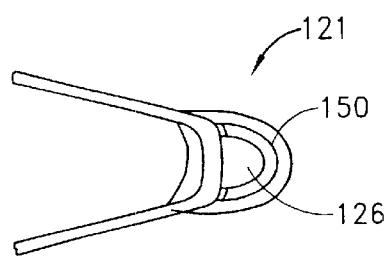
Figure 5H:
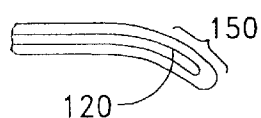
Figure 5I:
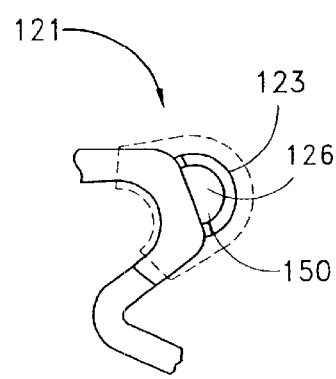
Figure 5J:
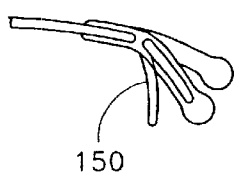
Figure 5K:
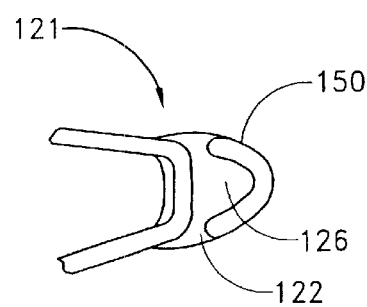
Figure 5L:
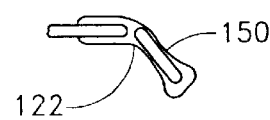
Figure 6A:
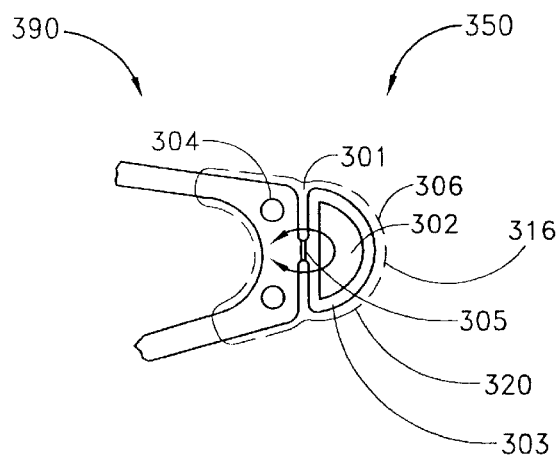
FIG. 6A is a plan view of a preferred embodiment of the hinged region of the haptic of FIG. 2A, 3A, or 4A in which the hinge is slotted and perforations are included.
Figure 6B:
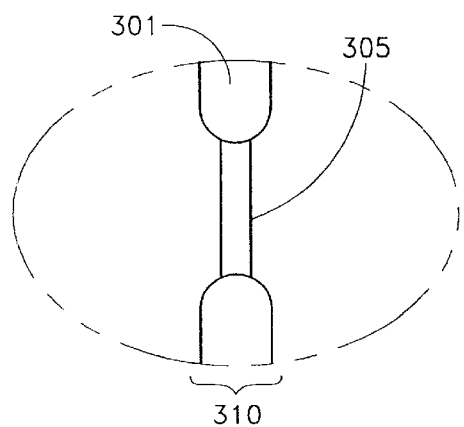
FIG. 6B is an enlarged view of the hinge region of 6A, showing the slots and the film frame bridge.
Figure 7A:
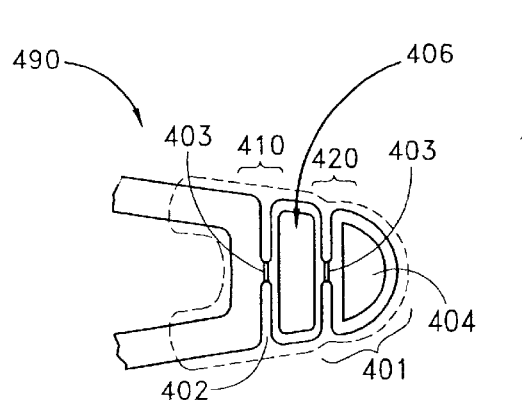
FIG. 7A is a plan view of a preferred embodiment in which the haptic includes two hinged segments.
Figure 7B:
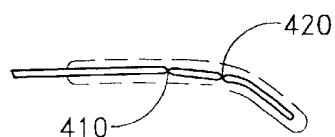
FIG. 7B is a side view of the two hinge segment haptic of FIG. 7A showing its curvature.

This embodiment may be formed into a hinge by breaking the high modulus material in the hinge region, so that the pieces are still connected by the low modulus coating. FIGS. 5C and D show scoring to provide a hinge region 120 next to a toe region 150. These regions may be flexed and broken at the score to yield an elastomeric hinge. FIGS. 5E and F show a loop or slot 126 and scoring to produce a hinge region 120 adjacent a toe region 150. FIGS. 5G and H show a notched or thinned region 123 at one end of the loop or slot 126, which temporarily supports the loop 126 in place during fabrication. FIGS. 5I and J show an indented notched or thinned region 123 at the other end of the loop or slot 126, which temporarily supports the loop 126 in place during fabrication. FIGS. 5K and L show a loop 126 formed such that both ends of the loop 126, are spaced from the foot 121 to form apertures 122.

Figure 8B:
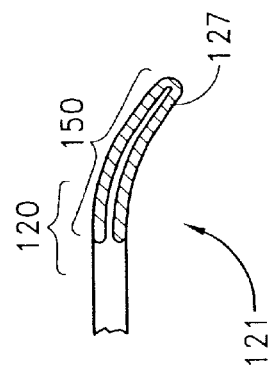
FIG. 8B is a side view of a preferred embodiment in which the hinge region is not broken, but is sculpted to be so thin that it has elastic qualities.
Figure 8C:
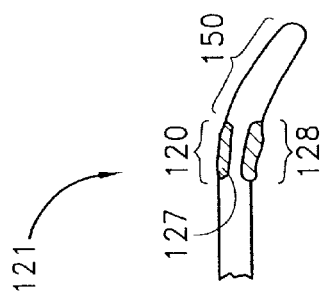
FIG. 8C is a side view of a preferred embodiment in which the whole toe is sculpted to be so thin that it has elastic qualities.
Figure 8A:
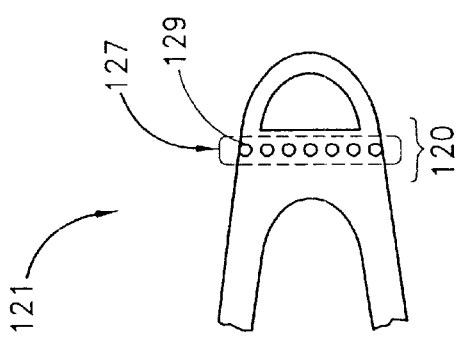
FIG. 8A is a plan view of a preferred embodiment in which the low modulus material only covers the hinge region.
Figure 10:
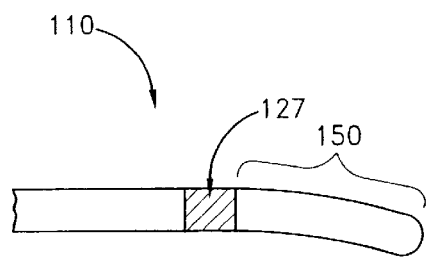
FIG. 10 is a side view of a preferred embodiment in which the hinge region uses a minimum of low modulus material.

FIG. 8B shows an embodiment in which the rigid material is sculpted away from one or both sides to produce a sculpted area 128 until the rigid material is so thin it becomes flexibly elastic to produce a hinge region 120. As shown in FIG. 5B, this sculpted area can additionally be coated with the elastomer 127 on one or both sides so that the elastomer 127 only covers the sculpted area 128 of the hinge 120. In figure 8C the whole toe region 150 is sculpted down until the rigid material becomes flexibly elastic. A farther, similar embodiment is shown in FIG. 8A in which apertures 129 are produced very close to each other and the elastomer 127 is added to just coat the aperture area 129, producing a hinge region 120, which may or may not be broken. The three types of hinges 120 of FIGS. A, B, and C would require minimal elastomer 127. Further embodiments of the hinge regions 120 are shown in FIGS. 5A–F, 6A–B, and 7A–B. An almost infinite variety of such hinges 120 can be contemplated. However, in reference to FIGS. 2A–C, generally the hinges 120 comprise an elastomeric element 127 which spans disconnected elements of the frame/haptic 110 to produce the flexible hinge 120. It is also envisioned that the hinge 120 can be fashioned without breakage by adding a hinging toe 150 to a haptic 110 using an elastomeric material 127 as shown in FIG. 10. In the preferred embodiment the hinges are all identical, however, clearly in alternative embodiments any of the embodiments of the hinges can be used alone or in combination. These resilient duplex material hinges exhibit a favorable lively memory characteristic so tat, when pivoted, they return to their original position as opposed to the typical monomaterial hinges that are "dead" and will tend to stay where they are put.

With reference to FIGS. 8A and 8B, a foot 121 with a minimal amount of elastomer 127 is provided. The foot region 121 comprises fenestrations 128 along the hinge region 120. The elastomer 127 may be added only within the perforations. Thereafter, the hinge region 120 may be broken to produce a toe 150 as mentioned before. Alternatively, the elastomer 127 can be coated over the toe 150 completely such that the elastomer 127 interconnects through the fenestrations 128 and around the frame to lock the assembly together.

With reference to FIG. 2, the hinge 120 can also comprise an elastomeric protuberance, or lip 300. The elastomeric lip 300 is composed of the same elastomeric material disclosed above. The elastomeric material is applied in such a way that it extends beyond the perimeter of the tip of the toe region 121, which can be accomplished through multiple dip coating or dip coating with a secondary elastomer with a different hardness. The lip 300 can be seen particularly well in FIGS. 3A and 3B. The elastomeric lip 300 provides a very gentle atraumatic interaction with the tissues of the anterior chamber angle. Therefore, it is anticipated that the interaction will cause a minimum of pressure to this very important region and, as an added benefit, there will be a minimum of discomfort to the patient.

With reference now to FIG. 6, a foot 350 arranged and configured in accordance with certain features, aspects and advantages of the present invention will be described in detail. The foot 350 comprises a hinge region 310 which separates the toe 320 from the rest of the foot 350. The hinge region comprises at least one gap 301 with a bridge 305. The bridge 305 is part of the film frame and can be ruptured after applying the elastomer 306. The toe 320 comprises a slot 302 which produces a thinner section of the high modulus material 303 within the toe 320. The foot 350 may also comprise one or more perforations, 304. The perforations 304, slot 302, and gaps 301 allow the elastomer 306 to intertwine and form a better anchor on the high modulus frame material. The perforations 304, slot 302, and gaps 301 also have the advantage of making the film frame or haptic 390 lighter and could be used in any embodiment of the haptic 390. The slot 302, perforations 304, and gaps 301 additionally function to make the whole film frame more flexible. The foot 350 further comprises a lip 316 comprising the elastomer which is the point of interaction with the eye tissue.

With reference to FIG. 7, a further embodiment of the haptic will be described. This embodiment has a plurality of hinges on each haptic, preferably two. The hinges 410 and 420 are formed in much the same way as the hinge 310 of FIG. 6, with the addition of a second internal hinge 410. Both hinges 410 and 420 comprise two gaps 402 and a bridge 403. The foot 450 comprises a slot 404 which produces a thinner region within the toe 401. The other hinged element of the haptic 490 may also comprise a slot 406 which has the same function as set out above in the discussion of FIG. 6A. In FIG. 713, it can be seen that using multiple hinges in concert with the springy frame, the angle of the haptic can be fine-tuned or modulated such that it will be less likely to touch the cornea.

With reference to FIG. 3, the frame/haptic itself 210 may also comprise one or more hinges 299. In reference to FIG. 3A, it can be seen that there is a secondary hinge region 299 in combination, between two feet 221, which permits folding of the film frame/haptic 210 to more easily insert it into the eye through a very small incision. A smaller incision permits quicker healing and a better optical outcome.

EXAMPLE 1

Making the Film Frame/haptic of the Preferred Embodiment

The process for making the film frame 110 of FIG. 2A–C will now be described.

The polypolyphenylsulfone. UDEL-R 5000 (0.002 inch) was acquired as an extruded film (WESTLAKE Plastics). A portion of the film was rolled out and held in place with a vacuum. The film frame 100 shape was cut by burning with a triple YAG laser in air and the holes, notches and/or scoring were also fabricated using the laser. Because the edges were rough, they. were polished using agitation polishing. For agitation polishing, the film frame was added to a jar with glass beads and a slurry of water, and $Al_2O_3$ or $SiO_2$. The polyphenylsulfone film frame was added and agitated at room temperature for 4 to 12 hours. The frames were removed and cleaned, then, the hinge regions were surface-treated by corona treatment. Corona treatment involves a discharge of 50,000 Volts at high frequency onto the treated area. The frame was then dip-coated in the discharge CF1135 primer and air dried for 0.5 to 1 hour. The elastomer, NUSIL MED 6400 dispersion parts A and B were mixed at a 1:1 ratio and dip coated on the feet by simply dipping the area where needed into mixed NUSIL MED 6400 dispersion and letting the elastomer dry 30 minutes at room temperature, then the elastomer was cured in a small 250–350° C. convection oven. Multiple dipping makes the area durable and uniform and more resilient. The final coating thickness measured about 0.001 to 0.002 inches but could be 0.0005 to 0.001 inches.

After curing of the elastomer, the high-modulus bridge which connects the toe to the foot was tested before and after rupturing the hinge. Rupturing was by multiple bending of the hinge until the toe was held onto the foot by the elastomer only. The test is described in Example 2.

EXAMPLE 2

Compression Testing

After samples were manufactured, hinge displacement testing was conducted on PPSU film frames (about 0.002 inch) coated with about 0.001 inch thick MED 6600 silicone skin. Hinge displacement testing is well know to one of skill in the art, however, the method of International standard ISO 11979-3 for ophthalmic implants/intraocular lenses was used. The IOL was mounted through the center line of the lens before and after breaking of the hinges. Then, a force is exerted such that the diameter is compressed a fixed amount. The displacement force is then measured. Displacement compression forces are for a 0.010 inch (¼ mm) and a 0.020 inch (½ mm) compression distance across the frame. The force measurements shown are in milligrams.

TABLE I

Compression testing

| | Displacement | |
| --- | --- | --- |
| | 0.010 inches | 0.020 inches |
| Non-broken frame* | 0.217 mg | 0.277 mg |
| After breaking* | 0.137 mg | 0.208 mg |
| | =37% less force | =25% less force |

*Note: it was observed that a visual estimate of the permanent "set" of the toe hinge position for unbroken hinges is about 25% but after breaking the hinge there was almost no discernable set.

This test shows that the pressure being put on the eye by a broken hinge is considerably less then that of an unbroken hinge. The broken hinge exerted at least a 25% reduced force. In addition, the broken hinge returned to its original position, showing it has good memory. It is envisioned that future improvements in design and processing can reduce these forces by as much as about 75% as needed.

Therefore, the IOL of the present invention presents a number of advantages. Firstly, it is lightweight and thin which reduces corneal chafing and pupillary block. In addition, because of the hinges and toes, it is capable of being inserted and resting on the anterior chamber angle with a minimum of damage to the tissues as well as a minimum of discomfort to the patient. The fact that it is a plate haptic eliminates the problem of synechiae, and it can be used in a phakic or aphakic eye.

The lens can be implanted into the eye using a variety of surgical implant techniques known in the art. Although the preferred embodiment is that the lens be implanted into the anterior chamber, using the anterior chamber angles, it can be envisioned that the lens could also be implanted in the posterior chamber.

Additionally, any combination of the materials used will result in a lens that can be sterilized by a variety of standard methods such as ethylene oxide (ETO) or steam autoclaving at 250° F. or any other acceptable method and the lens will show long term biocompatablity and hydrolytic stability.

While this invention has been described with respect to various specific examples and embodiments, it is to be understood that the invention is not limited thereto and that it can be variously practiced within the scope of the following claims:

What is claimed is:

1. An intraocular lens (IOL) comprising:
   an optic; and
   a haptic comprising:
      a pair of relatively more rigid elements formed of relatively higher modulus material, said pair of relatively more rigid elements separated from one another at a discontinuity; and
      a relatively less rigid element formed of relatively lower modulus material bridging said discontinuity.

2. The intraocular lens of claim 1, wherein bridged element allows for the relatively more rigid element to be rotationally to fit into the anterior chamber angle.

3. The intraocular lens of claim 1, wherein rotation of said bridged element causes stretching of the lower modulus material on the outside and compression on the inside of the hinge.

4. The intraocular lens of claim 1, wherein said intraocular lens comprises four separate relatively more rigid elements.

5. The intraocular lens of claim 1, wherein said higher modulus material is selected from the group consisting of: polyimide, polyetheretherketone, polycarbonate, polymethylpentene, polymethylmethyl methacrylate, polypropylene, polyvinylidene fluoride, polysulfone, and polyether sulfone.

6. The intraocular lens of claim 5, wherein said polyimide is KAPTON.

7. The intraocular lens of claim 5, wherein said higher modulus material is polyphenylsulfone (PPSU).

8. The intraocular lens of claim 1, wherein said higher modulus material is about 100,000 to about 500,000 psi/inch.

9. The intraocular lens of claim 8, wherein said higher modulus material is about 340,000 psi/inch.

10. The intraocular lens of claim 1, wherein said higher modulus material is less than or equal to about 0.01 inches thick.

11. The intraocular lens of claim 1, wherein said lower modulus material is an elastomer selected from the group consisting of: silicones, urethane, or hydrophilic acrylics.

12. The lens of claim 11, wherein said lower modulus material is a silicone.

13. The intraocular lens of claim 1, wherein said lower modulus material is about 100 to about 1000 psi.

14. The intraocular lens of claim 1, wherein said lower modulus material has a hardness of about 15 to 70 A scale.

15. The intraocular lens of claim 1, wherein said higher modulus material is 60 to 95 shore D.

16. The intraocular lens of claim 1, wherein said relatively more rigid elements comprise a frame.

17. The intraocular lens of claim 16, wherein said frame and haptic are formed from a single materially uniform piece.

18. The intraocular lens of claim 16, wherein said frame further comprises a rupturable hinge to allow for folding the intraocular lens.

19. The intraocular lens of claim 16, wherein said frame further comprises one or more additional haptics.

20. The intraocular lens of claim 16, wherein said lower modulus material completely covers said frame.

21. The intraocular lens of claim 1, wherein said haptic further comprises a slot.

22. The intraocular lens of claim 20, wherein said slot has an opening is open on one side of the hinge and wherein is bendable at the opening.

23. The intraocular lens of claim 21, wherein said haptic further comprises a groove and wherein is bendable at said groove.

24. The intraocular lens of claim 1, wherein said lens and said haptics are formed from a single materially uniform piece.

25. The intraocular lens of claim 1, wherein said haptic is broken at said discontinuity.

26. The intraocular lens of claim 1, wherein said optic is selected from the group consisting of a refractive lens, or an interference lens.

27. The intraocular lens of claim 1, wherein said haptic is attached to said optic externally.

28. The intraocular lens of claim 1, wherein said lower modulus material partially or completely covers said haptics.

29. The intraocular lens of claim 1, wherein said lower modulus material is extended toward the tip of said haptic to produce a softer contact point for the eye tissue.

30. The intraocular lens of claim 1, wherein said lower modulus material is applied by surface treatment and molding.

31. The intraocular lens of claim 30, wherein said surface treatment is a corona or plasma treatment.

32. The intraocular lens of claim 31, wherein said surface treatment is also for bonding of the optic onto the haptic.

33. The intraocular lens of claim 31, wherein said surface treatment is only for binding of the low modulus material.

34. The intraocular lens of claim 30, wherein said molding is selected from the group consisting of dip molding, cast molding, and injection molding.

35. A method of mounting the intraocular lens of claim 1 in the anterior chamber of an eye, comprising:
   supporting said lens on a plate haptic at the angle of said anterior chamber; and
   bending said haptic at a preferential hinge line to reduce pressure against said angle.

36. An intraocular lens frame, comprising:
   two plate haptic elements each comprising:
      a foot region and a toe region both formed of relatively higher modulus material; and
      a hinge connecting said toe region to said foot regions, said hinge formed of relatively lower modulus material.

37. The intraocular lens of claim 36 wherein rotation of the hinge causes stretching of the lower modulus material on the outside and compression on the inside of the hinge.

38. An intraocular lens comprising:
   an optic; and
   a haptic comprising a pair of stiff elements joined by a flexible element of different material.

39. A method for making an intraocular lens haptic, comprising:
   forming a frame;
   coating a location of said frame; and
   breaking said frame at said location.

40. A method of mounting a lens in the anterior chamber of an eye, comprising:
   supporting said lens on a plate haptic at the angle of said anterior chamber; and,
   bending said haptic at a preferential hinge line to reduce pressure against said angle.

* * * * *